United States Patent
Engelund et al.

(10) Patent No.: US 7,595,293 B2
(45) Date of Patent: Sep. 29, 2009

(54) STABLE PHARMACEUTICAL COMPOSITIONS

(75) Inventors: Dorthe Kot Engelund, Holte (DK); Tina Bjeldskov Pedersen, Ballerup (DK); Claude Bonde, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 273 days.

(21) Appl. No.: 11/244,497

(22) Filed: Oct. 3, 2005

(65) Prior Publication Data

US 2006/0084605 A1    Apr. 20, 2006

Related U.S. Application Data

(63) Continuation of application No. PCT/DK2004/000233, filed on Apr. 2, 2004.

(60) Provisional application No. 60/462,604, filed on Apr. 14, 2003.

(30) Foreign Application Priority Data

Apr. 11, 2003   (DK) ............................... 2003 00579

(51) Int. Cl.
   *C07K 14/00* (2006.01)
(52) U.S. Cl. ......................................... 514/2; 530/350
(58) Field of Classification Search ................ 530/350; 514/2
   See application file for complete search history.

(56) References Cited

U.S. PATENT DOCUMENTS

| 6,191,102 | B1 | 2/2001 | DiMarchi et al. |
| 6,358,924 | B1 * | 3/2002 | Hoffmann ..................... 514/12 |
| 2002/0049153 | A1 | 4/2002 | Bridon et al. |
| 2002/0128181 | A1 | 9/2002 | Nauck et al. |

FOREIGN PATENT DOCUMENTS

| WO | 90/12029 | 4/1990 |
| WO | 98/08872 | 3/1998 |
| WO | 99/43361 | 2/1999 |
| WO | 9943341 | 2/1999 |
| WO | 00/41546 | 1/2000 |
| WO | 00/37098 | 6/2000 |
| WO | 0037098 | 6/2000 |
| WO | 01/10446 | 2/2001 |
| WO | 02/46227 | 6/2002 |
| WO | 02/072135 | 9/2002 |
| WO | 03/002136 | 1/2003 |
| WO | 03/103572 | 6/2003 |

OTHER PUBLICATIONS

Blundell, T L—Springer Verlag—1983—vol. 66—pp. 37-56.
Sendorff, R I et al—J Pharm Sci—1998—vol. 87—pp. 183-189.

* cited by examiner

*Primary Examiner*—Karen Cochrane Carlson
(74) *Attorney, Agent, or Firm*—Shelby J. Walker

(57) ABSTRACT

Pharmaceutical composition for parenteral administration comprising a glucagon-like peptide and human serum albumin or a variant thereof.

52 Claims, No Drawings

SEQUENCE LISTING

```
<160> NUMBER OF SEQ ID NOS: 1

<210> SEQ ID NO 1
<211> LENGTH: 585
<212> TYPE: PRT
<213> ORGANISM: homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45
```

```
Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460
```

-continued

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580             585
```

STABLE PHARMACEUTICAL COMPOSITIONS

CROSS REFERENCE TO RELATED APPLICATIONS

This application is a continuation of International Application No. PCT/DK2004/000233, filed Apr. 2, 2004, which claims priority to Danish Patent Application No. PA 2003 00579, filed Apr. 11, 2003, and U.S. patent application Ser. No. 60/462,604, filed Apr. 14, 2003.

FIELD OF THE INVENTION

The present invention relates to the field of pharmaceutical compositions. More specifically the invention pertains to pharmaceutical compositions for parenteral administration, which comprises a glucagon-like peptide and human serum albumin.

BACKGROUND OF THE INVENTION

Therapeutic peptides are widely used in medical practise. Pharmaceutical compositions of such therapeutic peptides must have a shelf life of several years in order to be suitable for common use. However, peptide compositions are inherently unstable due to sensitivity towards chemical and physical degradation. Chemical degradation involves change of covalent bonds, such as oxidation, hydrolysis, racemization or crosslinking. Physical degradation involves conformational changes relative to the native structure of the peptide, i.e. secondary and tertiary structure, such as aggregation, precipitation or adsorption to surfaces.

Glucagon has been used for decades in medical practise within diabetes and several glucagon-like peptides are being developed for various therapeutic indications. The preproglucagon gene encodes glucagon as well as glucagon-like peptide 1 (GLP-1) and glucagon-like peptide 2 (GLP-2). GLP-1 analogs and derivatives as well as the homologous lizard peptide, exendin-4, are being developed for the treatment of hyperglycemia within type 2 diabetes. GLP-2 is potentially useful in the treatment of gastrointestinal diseases. However, all these peptides encompassing 29-39 amino acids have a high degree of homology and they share a number of properties, notably their tendency to aggregate and formation of insoluble fibrils. This property seems to encompass a transition from a predominant alpha-helix conformation to beta-sheets (Blundell T. L. (1983) The conformation of glucagon. In: Lefébvre P. J. (Ed) Glucagon I. Springer Verlag, pp 37-55, Senderoff R. I. et al., J. Pharm. Sci. 87 (1998)183-189). Aggregation of the glucagon-like peptides are mainly seen when solutions of the peptides are stirred or shaken, at the interface between solution and gas phase (air), and at contact with hydrophobic surfaces such as Teflon®.

Thus, pharmaceutical compositions of the glucagon-like peptides must often be added various excipients in order to improve the stability. Shelf life of liquid parenteral formulations of these peptides must be at least a year, preferably longer. The in-use period where the product may be transported and shaken daily at ambient temperature preferably should be several weeks. Thus, there is a need for pharmaceutical compositions of glucagon-like peptides which have improved stability.

We have unexpectedly found human serum albumin to be an excipient that can improve the stability of pharmaceutical compositions containing a glucagon-like peptide.

WO 99/43341 and WO 03/02136 discloses certain pharmaceutical formulations comprising GLP-1 derivatives. WO 00/37098 discloses formulations comprising GLP-1 at pH from 8.2 to 8.8. WO 00/41546 discloses formulations comprising exendin-4, a buffer, an isotonic agent and pH between 3 and 7.

WO 01/10446 discloses formulations of the cytotoxic drug estramustine phosphate comprising albumin to protect against side-effects at the site of injection. WO 90/12029 discloses the use of serum albumin in lyophilized pharmaceutical formulations. WO 02/72135 discloses liquid preparations of interferon a comprising serum albumin.

The present invention is based on the finding that pharmaceutical compositions of glucagon-like peptides comprising human serum albumin have increased stability.

SUMMARY OF THE INVENTION

The present invention relates to pharmaceutical compositions for parenteral administration comprising a glucagon-like peptide and human serum albumin or a variant thereof.

DEFINITIONS

The following is a detailed definition of the terms used in the specification.

The term "effective amount" as used herein means a dosage which is sufficient to be effective for the treatment of the patient compared with no treatment.

The term "pharmaceutical composition" as used herein means a product comprising an active compound or a salt thereof together with pharmaceutical excipients such as buffer, preservative, and optionally a tonicity modifier and/or a stabilizer. Thus a pharmaceutical composition is also known in the art as a pharmaceutical formulation.

The term "buffer" as used herein refers to a chemical compound in a pharmaceutical composition that reduces the tendency of pH of the composition to change over time as would otherwise occur due to chemical reactions. Buffers include chemicals such as sodium acetate, sodium carbonate, citrate, glycylglycine, histidine. lysine, arginin, sodium phosphate, TRIS, glycine and sodium citrate or mixtures thereof.

The term "preservative" as used herein refers to a chemical compound which is added to a pharmaceutical composition to prevent or delay microbial activity (growth and metabolism). Examples of pharmaceutically acceptable preservatives are phenol, m-cresol, or mixtures thereof.

The term "isotonic agent" as used refers to a chemical compound in a pharmaceutical composition that serves to modify the osmotic pressure of the pharmaceutical composition so that the osmotic pressure becomes closer to that of human plasma. Isotonic agents may be selected from a variety of chemicals such as salts and small organic molecules, e.g. NaCl, glycerol, mannitol, sorbitol etc.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term "analogue" as used herein referring to a peptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. A simple system is used to describe analogues: For example $Arg^{34}$-GLP-1(7-37) designates a GLP-1(7-37) analogue wherein the naturally occuring lysine at position 34 has been substituted with arginine. Another example is HSA(2-585) which denotes an analogue of human serum albumin wherein the terminal Asp residue in human serum albumin (SEQ ID No. 1) has been deleted. All amino acids for which the optical isomer is not stated is to be understood to mean the L-isomer. Likewise, standard single letter abbreviation for amino acids are used according to IUPAC-IUB nomenclature.

The term "derivative" as used herein in relation to a parent peptide means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, pegylations and the like. An examples of a derivative of GLP-1(7-37) is $Arg^{34}$, $Lys^{26}(N^\epsilon$-($\gamma$-Glu($N^\alpha$-hexadecanoyl)))-GLP-1(7-37).

The term "a fragment thereof" as used herein in relation to a peptide means any fragment of the peptide having at least 20% of the amino acids of the parent peptide. Thus, for human serum albumin a fragment would comprise at least 117 amino acids as human serum albumin has 585 amino acids. In one embodiment the fragment has at least 35% of the amino acids of the parent peptide. In another embodiment the fragment has at least 50% of the amino acids of the parent peptide. In another embodiment the fragment has at least 75% of the amino acids of the parent peptide.

The term "glucagon-like peptide" as used herein means the glucagon family of peptides, exendins and variants thereof. The glucagon family of peptides are encoded by the preproglucagon gene and encompasses three small peptides with a high degree of homology, i.e. glucagon(1-29), GLP-1(1-37) and GLP-2(1-33). Exendins are peptides expressed in lizards and like GLP-1 they are insulinotropic. Examples of exendins are exendin-4 and exendin-3.

The term "variant" as used herein in relation to a peptide means a modified peptide which is an analogue of the parent peptide, a fragment of the parent peptide, a derivative of the parent peptide, an analogue thereof or a fragment thereof, or a derivative of an analog of the parent peptide. The parent peptide being the unmodified peptide, i.e. for the peptide $Arg^{34}$, $LYS^{26}(N^\epsilon$-($\gamma$-Glu($N^\alpha$-hexadecanoyl)))-GLP-1(7-37), the corresponding parent peptide is GLP-1(7-37).

The term "stable exendin-4 compound" as used herein means a chemically modified exendin-4(1-39), i.e. an analogue or a derivative which exhibits an in vivo plasma elimination half-life of at least 10 hours in man, as determined by the following method. The method for determination of plasma elimination half-life of an exendin-4 compound in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g. Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51):A143, 2000. Derived pharmacokinetic parameteres are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life. The term "DPP-IV protected exendin-4 compound" as used herein means an exendin-4 compound which has been chemically modified to render said compound resistant to the plasma peptidase dipeptidyl aminopeptidase-4 (DPP-IV).

The term "immunomodulated exendin-4 compound" as used herein means an exendin-4 compound which is an analogue or a derivative of exendin-4(1-39) having a reduced immune response in humans as compared to exendin-4(1-39). The method for assessing the immune response is to measure the concentration of antibodies reactive to the exendin-4 compound after 4 weeks of treatment of the patient.

The term "isoelectric point" as used herein means the pH value where the overall net charge of a macromolecule such as a peptide is zero. In peptides there may be many charged groups, and at the isoelectric point the sum of all these charges is zero. At a pH above the isoelectric point the overall net charge of the peptide will be negative, whereas at pH values below the isoelectric point the overall net charge of the peptide will be positive.

The term "reconstituted" as used herein referring to a pharmaceutical composition means an aqueous composition which has been formed by the addition of water or an appropriate aqueous solution to a solid material comprising the active pharmaceutical ingredient. Pharmaceutical compositions for reconstitution are applied where a liquid composition with acceptable shelf-life cannot be produced. An example of a reconstituted pharmaceutical composition is the solution which results when adding water or an appropriate aqueous solution to a freeze dried composition. The solution is often for parenteral administration and thus water for injection or any other appropriate solvent are used for reconstituting the solid material.

The term "pharmaceutical" as used herein with reference to a composition means that it is useful for treating a disease or disorder.

The term "pharmaceutically acceptable" as used herein means suited for normal pharmaceutical applications, i.e. giving rise to no adverse events in patients etc.

DESCRIPTION OF THE INVENTION

In a first aspect the invention relates to a pharmaceutical composition for parenteral administration, which comprises a glucagon-like peptide, human serum albumin or a variant thereof, a pharmaceutically acceptable buffer, a pharmaceutically acceptable preservative, and optionally an isotonic agent and/or a stabilizer.

In a second aspect the invention relates to a pharmaceutical composition for parenteral administration, which comprises a glucagon-like peptide, human serum albumin or a variant thereof, a pharmaceutically acceptable buffer, a pharmaceutically acceptable preservative, and optionally an isotonicγ agent and/or a stabilizer, said pharmaceutical composition or a reconstituted solution of said pharmaceutical composition having a pH from 6.5 to pH 9.0.

In a third aspect the invention relates to a pharmaceutical composition for parenteral administration, which comprises a glucagon-like peptide, human serum albumin or a variant thereof, a pharmaceutically acceptable buffer, a pharmaceutically acceptable preservative, and optionally an isotonicγ agent and/or a stabilizer, said composition being a solution.

In a further aspect the invention relates to a pharmaceutical composition for parenteral administration, which comprises a glucagon-like peptide, human serum albumin or a variant thereof, a pharmaceutically acceptable buffer, a pharmaceutically acceptable preservative, In a further aspect the invention relates to a pharmaceutical composition for parenteral administration, which comprises a glucagon-like peptide, human serum albumin or a variant thereof, a pharmaceutically acceptable buffer, a pharmaceutically acceptable preservative, and optionally an isotonicγ agent and/or a stabilizer, said composition being a solid.

In a further aspect the invention relates to a method of treatment of hyperglycemia comprising parenteral administration of an effective amount of a pharmaceutical composition for parenteral administration, which comprises a glucagon-like peptide, human serum albumin or a variant thereof, a pharmaceutically acceptable buffer, a pharmaceutically acceptable preservative, and optionally an isotonicγ agent and/or a stabilizer.

In a further aspect the invention relates to a method of treatment of hyperglycemia comprising parenteral administration of an effective amount of a pharmaceutical composition for parenteral administration, which comprises a glucagon-like peptide, human serum albumin or a variant thereof, water, a pharmaceutically acceptable buffer, a pharmaceutically acceptable preservative, and optionally an isotonicγ agent and/or a stabilizer.

In a further aspect the invention relates to the use of a glucagon-like peptide and human serum albumin or a variant thereof for the manufacture of a pharmaceutical composition for parenteral administration, said composition comprising a glucagon-like peptide, human serum albumin or a variant thereof, a pharmaceutically acceptable buffer, a pharmaceutically acceptable preservative, and optionally an isotonicγ agent and/or a stabilizer.

In a further aspect the invention relates to the use of a glucagon-like peptide and human serum albumin or a variant thereof for the manufacture of a pharmaceutical composition for parenteral administration, said composition comprising a glucagon-like peptide, human serum albumin or a variant thereof, water, a pharmaceutically acceptable buffer, a pharmaceutically acceptable preservative, and optionally an isotonicγ agent and/or a stabilizer.

In one embodiment of the invention the pharmaceutical formulation is an aqueous formulation, i.e. a formulation comprising water. Such formulation is typically a solution or a suspension. In a further embodiment of the invention the pharmaceutical formulation is an aqueous solution. In a further embodiment of the invention the water or aqueous solution used for reconstitution is water for injection or an aqueous solvent prepared using water for injection. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds the solvent prior to use.

In another embodiment of the invention the pharmaceutical composition or a reconstituted solution of said pharmaceutical composition has a pH from 7.0 to 8.5.

In another embodiment of the invention the pharmaceutical composition or a reconstituted solution of said pharmaceutical composition has a pH from 7.2 to 8.0.

Pharmaceutical compositions containing a glucagon-like peptide according to the present invention may be administered parenterally to patients in need of such treatment. Parenteral administration may be performed by subcutaneous injection, intramuscular injection, or intraveneous injection by means of a syringe, optionally a pen-like syringe. Alternatively administration can be performed by infusion, e.g. by use of an infusion pump.

In one embodiment of the invention the human serum albumin or a variant thereof is produced by recombinant DNA technology.

In another embodiment of the invention the human serum albumin or a variant thereof is a human serum albumin variant. In one embodiment of the invention the human serum albumin variant is a fragment of human serum albumin. In another embodiment of the invention the human serum albumin variant has reduced binding affinities towards copper and nickel as compared to the corresponding binding affinities of human serum albumin towards copper and nickel. In another embodiment of the invention the human serum albumin variant is a fragment of human serum albumin. In another embodiment of the invention the human serum albumin variant is a C-terminal fragment. In another embodiment of the invention the human serum albumin variant is a N-terminal fragment. In another embodiment of the invention the human serum albumin variant comprises more than 500 amino acid residues. In another embodiment of the invention the human serum albumin variant comprises a modification of the Asp-Ala-His-Lys N-terminal sequence of human serum albumin. In another embodiment of the invention the human serum albumin variant comprises at least one amino acid deletion among the three N-terminal amino acid residues Asp-Ala-His in the N-terminal of human serum albumin. In another embodiment of the invention the modification of the Asp-Ala-His-Lys N-terminal sequence of human serum albumin is an N-terminal extension, such as Glu$^{-3}$,Ala$^{-2}$,Glu$^{-1}$,Phe$^{0}$-HSA (1-585) or an N-terminal fragment thereof. In another embodiment of the invention the human serum albumin variant is selected from the group consisting of HSA(2-585), HSA(3-585), HSA(4-585), Asp-Ala-HSA(4-585), Xaa$^{3}$-HSA(1-585) where Xaa$^{3}$ is an amino acid residue which has substituted the His residue occupying position 3 in native HSA, and fragments thereof.

In another embodiment of the present invention the concentration of human serum albumin or a variant thereof is less than 10% w/v. In another embodiment of the invention the concentration of human serum albumin or a variant thereof is less than 5% w/v, or less than 1% w/v, or less than 0.5% w/v, or less than 0.2% w/v, or less than 0.1% w/v, or less than 0.001% w/v.

In one embodiment of the invention the isoelectric point of the glucagon-like peptide is from 3.0 to 7.0, from 4.0 to 6.0, from 4.0 to 5.0, or from 4.3 to 4.8.

In another embodiment of the present invention the glucagon-like peptide is GLP-1, a GLP-1 analogue, a derivative of GLP-1 or a derivative of a GLP-1 analogue.

In another embodiment of the present invention the GLP-1 analogue is selected from the group consisting of Gly$^{8}$-GLP-1(7-36)-amide, Gly$^{8}$-GLP-1(7-37), Val$^{8}$-GLP-1(7-36)-amide, Val$^{8}$-GLP-1(7-37), Val$^{8}$Asp$^{22}$-GLP-1(7-36)-amide, Val$^{8}$Asp$^{22}$-GLP-1(7-37), Val$^{8}$Glu$^{22}$-GLP-1(7-36)-amide, Val$^{8}$Glu$^{22}$-GLP-1(7-37), Val$^{8}$Lys$^{22}$-GLP-1(7-36)-amide, Val$^{8}$Lys$^{22}$-GLP-1(7-37), Val$^{8}$Arg$^{22}$-GLP-1(7-36)-amide, Val$^{8}$Arg$^{22}$-GLP-1(7-37), Val$^{8}$His$^{22}$-GLP-1(7-36)-amide, Val$^{8}$His$^{22}$-GLP-1(7-37), Val$^{8}$Trp$^{19}$Glu$^{22}$-GLP-1(7-37), Val$^{8}$Glu$^{22}$Val$^{25}$-GLP-1(7-37), Val$^{8}$Tyr$^{16}$Glu$^{22}$-GLP-1(7-37), Val$^{8}$Trp$^{16}$Glu$^{22}$-GLP-1(7-37), Val$^{8}$Leu$^{16}$Glu$^{22}$-GLP-1(7-

37), Val$^8$Tyr$^{18}$Glu$^{22}$-GLP-1(7-37), Val$^8$Glu$^{22}$His$^{37}$-GLP-1 (7-37), Val$^8$Glu$^{22}$Ile$^{33}$-GLP-1(7-37), Val$^8$Trp$^{16}$Glu$^{22}$Val$^{25}$Ile$^{33}$-GLP-1(7-37), Val$^8$Trp$^{16}$Glu$^{22}$Ile$^{33}$-GLP-1(7-37), Val$^8$Glu$^{22}$Val$^{25}$Ile$^{33}$-GLP-1(7-37), Val$^8$Trp$^{16}$Glu$^{22}$Val$^{25}$-GLP-1(7-37), analogues thereof and derivatives of any of these.

In another embodiment of the present invention the derivative of GLP-1 or a derivative of a GLP-1 analogue has a lysine residue, such as one lysine, wherein a lipophilic substituent optionally via a spacer is attached to the epsilon amino group of said lysine.

In another embodiment of the present invention the lipophilic substituent has from 8 to 40 carbon atoms, preferably from 12 to 24 carbon atoms, e.g. 14 to 18 carbon atoms.

In another embodiment of the present invention the spacer is present and is selected from an amino acid, e.g. beta-Ala, L-Glu, or aminobutyroyl.

In another embodiment of the present invention the glucagon-like peptide is a DPPIV-protected glucagon-like peptide.

In another embodiment of the present invention the glucagon-like peptide is a plasma stable glucagon-like peptide.

In another embodiment of the present invention the glucagon-like peptide is a derivative of a GLP-1 analogue which is Arg$^{34}$, Lys$^{26}$(N$^\epsilon$-(γ-Glu(N$^\alpha$-hexadecanoyl)))-GLP-1(7-37).

In another embodiment of the present invention the glucagon-like peptide is aGLP-1 peptide which has from 31 to 43 amino acid residues, preferable from 33 to 41 amino acid residues, even more preferable from 35 to 39 amino acid residues.

In another embodiment of the present invention the glucagon-like peptide is a GLP-1 peptide and the pharmaceutical composition or a reconstituted composition thereof has a glucagon-like peptide concentration from 0.1 mg/mL to 50 mg/mL, from 0.1 mg/mL to 25 mg/mL, from 1 mg/mL to 25 mg/mL, from 1 mg/mL to 10 mg/mL, or from 3 mg/mL to 8 mg/mL.

In one embodiment of the present invention the glucagon-like peptide is GLP-2, a GLP-2 analogue, a derivative of GLP-2 or a derivative of a GLP-2 analogue.

In another embodiment of the present invention the derivative of GLP-2 or a derivative of a GLP-2 analogue has a lysine residue, such as one lysine, wherein a lipophilic substituent optionally via a spacer is attached to the epsilon amino group of said lysine.

In another embodiment of the present invention the lipophilic substituent has from 8 to 40 carbon atoms, preferably from 12 to 24 carbon atoms, e.g. 14 to 18 carbon atoms.

In another embodiment of the present invention the spacer is present and is selected from an amino acid, e.g. beta-Ala, L-Glu, aminobutyroyl.

In another embodiment of the present invention the glucagon-like peptide has from 27 to 39 amino acid residues, preferable from 29 to 37 amino acid residues, even more preferable from 31 to 35 amino acid residues.

In another embodiment of the present invention the glucagon-like peptide is a GLP-2 peptide and the pharmaceutical composition or a reconstituted composition thereof has a glucagon-like peptide concentration from 0.1 mg/mL to 100 mg/mL, from 0.1 mg/mL to 25 mg/mL, or from 1 mg/mL to 25 mg/mL.

In one embodiment of the present invention the glucagon-like peptide is exendin-4, an exendin-4 analogue, a derivative of exendin-4, or a derivative of an exendin-4 analogue.

In another embodiment of the present invention the glucagon-like peptide is exendin-4.

In another embodiment of the present invention the derivative of exendin-4 or derivative of an exendin-4 analogue is acylated or pegylated.

In another embodiment of the present invention the glucagon-like peptide is a stable exendin-4 compound.

In another embodiment of the present invention the glucagon-like peptide is a DPP-IV protected exendin-4 compound.

In another embodiment of the present invention the glucagon-like peptide is an immunomodulated exendin-4 compound.

In another embodiment of the present invention the derivative of exendin-4 or derivative of an exendin-4 analogue has a lysine residue, such as one lysine, wherein a lipophilic substituent optionally via a spacer is attached to the epsilon amino group of said lysine.

In another embodiment of the present invention the lipophilic substituent has from 8 to 40 carbon atoms, preferably from 12 to 24 carbon atoms, e.g. 14 to 18 carbon atoms.

In another embodiment of the present invention the spacer is present and is selected from an amino acid, e.g. beta-Ala, L-Glu, or aminobutyroyl.

In another embodiment of the present invention the glucagon-like peptide is an exendin-4 peptide which has from 30 to 48 amino acid residues, from 33 to 45 amino acid residues, preferable from 35 to 43 amino acid residues, even more preferable from 37 to 41 amino acid residues.

In another embodiment of the present invention the glucagon-like peptide is an exendin-4 peptide and the pharmaceutical composition or a reconstituted composition thereof has a glucagon-like peptide concentration from 5 μg/mL to 10 mg/mL, from 5 μg/mL to 5 mg/mL, from 5 μg/mL to 5 mg/mL, from 0.1 mg/mL to 3 mg/mL, or from 0.2 mg/mL to 1 mg/mL.

In one embodiment of the present invention the glucagon-like peptide is glucagon, a glucagon analogue or a derivative thereof.

In another embodiment of the present invention the glucagon-like peptide is Arg$^{34}$, Lys$^{26}$(N$^\epsilon$-(γ-Glu(N$^\alpha$-hexadecanoyl)))-GLP-1(7-37) and said human serum albumin or a variant thereof is recombinant human serum albumin.

In another embodiment of the present invention the concentration of Arg$^{34}$, Lys$^{26}$(N$^\epsilon$-(γ-Glu(N$^\alpha$-hexadecanoyl)))-GLP-1(7-37) is in the range from from 3 mg/mL to 8 mg/mL and the concentration of recombinant human serum albumin is in the range from 0.001% w/v to 10% w/v.

In one embodiment of the present invention the buffer is orhto-phosphate, TRIS, glycine, N-glycylglycine, citrate sodium acetate, sodium carbonate, glycylglycine, histidine, lysine, arginin, sodium phosphate, and sodium citrate or mixtures thereof. In another embodiment of the present invention the buffer is HEPES, BICINE or TRICINE.

In one embodiment of the present invention the preservative is phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof.

In another embodiment of the present invention the isotonicity agent is present.

In another embodiment of the present invention the isotonicity agent is sodium chloride, xylitol, mannitol, sorbitol, glycerol, glucose, maltose, sucrose, L-glycine, L-histidine, arginine, lysine, isoleucine, aspartic acid, tryptophan, threonine, polyethyleneglycol, propylene glycol or mixtures thereof.

In another embodiment of the present invention the isotonicity agent is selected from the group consisting of mannitol, sorbitol, glycerol, propylene glycol and mixtures thereof.

In another embodiment of the present invention the pharmaceutical composition further comprises a stabiliser.

In a further embodiment of the invention the formulation further comprises a stabiliser selected from the group of high molecular weight polymers or low molecular compounds.

In a further embodiment of the invention the stabilizer is selected from polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment of the invention. In a preferred embodiment of the invention the stabiliser is selected from the group consisting of L-histidine, imidazole and arginine.

In another embodiment of the present invention the stabiliser is selected from the group consisting of PEG 3350, polyvinylalcohol, polyvinylpyrrolidone, carboxy-methylcellulose, sodium chloride, L-glycine, L-histidine, imidazole, L-arginine, L-lysine, L-isoleucine, L-aspartic acid, L-tryptophan, L-threonine and mixtures thereof.

In a further embodiment of the invention the formulation further comprises a chelating agent.

In a further embodiment of the invention the chelating agent is selected from salts of ethlenediaminetetraacetic acid (EDTA), citric acid, and aspartic acid, and mixtures thereof. Each one of these specific chelating agents constitutes an alternative embodiment of the invention.

In another embodiment of the present invention the pharmaceutical composition further comprises a surfactant. In a further embodiment of the invention the surfactant is selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N, N-dimethyl-3-ammonio-1-propanesulfonate, anionic (alkyl-arylsulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)- derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N, N-dimethylammonio-1 -propanesulfonates, 3-cholamido-1-propyldimethylammonio-l -propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives-(e.g. sodium tauro-dihydrofusidate etc.), long-chain falty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of excipients such as preservatives, isotonic agents and surfactants in pharmaceutical compositions is well-known to the skilled person. For convenience reference is made to Remington: *The Science and Practice of Pharmacy*, 19$^{th}$ edition, 1995.

In one embodiment of the invention the GLP-2 peptide is selected from the list consisting of:

K30R-GLP-2(1-33); S5K-GLP-2(1-33); S7K-GLP-2(1-33); D8K-GLP-2(1-33); E9K-GLP-2(1-33); M10K-GLP-2(1-33); N11K-GLP-2(1-33); T12K-GLP-2(1-33); I13K-GLP-2 (1-33); L14K-GLP-2(1-33); D15K-GLP-2(1-33); N16K-GLP-2(1-33); L17K-GLP-2(1-33); A18K-GLP-2(1-33); D21K-GLP-2(1-33); N24K-GLP-2(1-33); Q28K-GLP-2(1-33); S5K/K30R-GLP-2(1-33); S7K/K30R-GLP-2(1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); I13K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33);

D3E/S5K/K30R/D33E-GLP-2(1-33); D3E/S7K/K30R/D33E-GLP-2(1-33);

D3E/D8K/K30R/D33E-GLP-2(1-33); D3E/E9K/K30R/D33E-GLP-2(1-33);

D3E/M10K/K30R/D33E-GLP-2(1-33); D3E/N11K/K30R/D33E-GLP-2(1-33);

D3E/T12K/K30R/D33E-GLP-2(1-33); D3E/I13K/K30R/D33E-GLP-2(1-33);

D3E/L14K/K30R/D33E-GLP-2(1-33); D3E/D15K/K30R/D33E-GLP-2(1-33);

D3E/N16K/K30R/D33E-GLP-2(1-33); D3E/L17K/K30R/D33E-GLP-2(1-33);

D3E/A18K/K30R/D33E-GLP-2(1-33); D3E/D21K/K30R/D33E-GLP-2(1-33);

D3E/N24K/K30R/D33E-GLP-2(1-33); D3E/Q28K/K30R/D33E-GLP-2(1-33); and derivatives thereof.

In one embodiment of the invention the GLP-2 derivative is selected from the group consisting of S5K(3-(hexadecanoylamino)propionyl)-GLP-2(1-33);
S7K(3-(hexadecanoylamino)propionyl)-GLP-2(1-33);
D8K(3-(hexadecanoylamino)propionyl)-GLP-2(1-33);
E9K(3-(hexadecanoylamino)propionyl)-GLP-2(1-33);
M10K(3-(hexadecanoylamino)propionyl)-GLP-2(1-33);
N11K(3-(hexadecanoylamino)propionyl)-GLP-2(1-33);
T12K(3-(hexadecanoylamino)propionyl)-GLP-2(1-33);
I13K(3-(hexadecanoylamino)propionyl)-GLP-2(1-33);

L14K(3-(hexadecanoylamino)propionyl)-GLP-2(1-33);
D15K(3-(hexadecanoylamino)propionyl)-GLP-2(1-33);
N16K(3-(hexadecanoylamino)propionyl)-GLP-2(1-33);
L17K(3-(octanoylamino)propionyl)-GLP-2(1-33);
L17K(3-(nonanoylamino)propionyl)-GLP-2(1-33);
L17K(3-(decanoylamino)propionyl)-GLP-2(1-33);
L17K(3-(undecanoylamino)propionyl)-GLP-2(1-33);
L17K(3-(dodecanoylamino)propionyl)-GLP-2(1-33);
L17K(3-(tridecanoylamino)propionyl)-GLP-2(1-33);
L17K(3-(tetradecanoylamino)propionyl)-GLP-2(1-33);
L17K(3-(pentadecanoylamino)propionyl)-GLP-2(1-33);
L17K(3-(hexadecanoylamino)propionyl)-GLP-2(1-33);
L17K(3-(heptadecanoylamino)propionyl)-GLP-2(1-33);
L17K(3-(octadecanoylamino)propionyl)-GLP-2(1-33);
L17K(3-(nonadecanoylamino)propionyl)-GLP-2(1-33);
L17K(3-(eicosanoylamino)propionyl)-GLP-2(1-33);
L17K((S)-4-carboxy-4-(octanoylamino)butanoyl)-GLP-2(1-33);
L17K((S)-4-carboxy-4-(nonanoylamino)butanoyl)-GLP-2(1-33);
L17K((S)-4-carboxy-4-(decanoylamino)butanoyl)-GLP-2(1-33);
L17K((S)-4-carboxy-4-(undecanoylamino)butanoyl)-GLP-2(1-33);
L17K((S)-4-carboxy-4-(dodecanoylamino)butanoyl)-GLP-2(1-33);
L17K((S)-4-carboxy-4-(tridecanoylamino)butanoyl)-GLP-2(1-33);
L17K((S)-4-carboxy-4-(tetradecanoylamino)butanoyl)-GLP-2(1-33);
L17K((S)-4-carboxy-4-(pentadecanoylamino)butanoyl)-GLP-2(1-33);
L17K((S)-4-carboxy-4-(hexadecanoylamino)butanoyl)-GLP-2(1-33);
L17K((S)-4-carboxy-4-(heptadecanoylamino)butanoyl)-GLP-2(1-33);
L17K((S)-4-carboxy-4-(octadecanoylamino)butanoyl)-GLP-2(1-33);
L17K((S)-4-carboxy-4-(nonadecanoylamino)butanoyl)-GLP-2(1-33);
L17K((S)-4-carboxy-4-(eicosanoylamino)butanoyl)-GLP-2(1-33);
L17K(4-(octanoylamino)butanoyl)-GLP-2(1-33);
L17K(4-(nonanoylamino)butanoyl)-GLP-2(1-33);
L17K(4-(decanoylamino)butanoyl)-GLP-2(1-33);
L17K(4-(undecanoylamino)butanoyl)-GLP-2(1-33);
L17K(4-(dodecanoylamino)butanoyl)-GLP-2(1-33);
L17K(4-(tridecanoylamino)butanoyl)-GLP-2(1-33);
L17K(4-(tetradecanoylamino)butanoyl)-GLP-2(1-33);
L17K(4-(pentadecanoylamino)butanoyl)-GLP-2(1-33);
L17K(4-(hexadecanoylamino)butanoyl)-GLP-2(1-33);
L17K(4-(heptadecanoylamino)butanoyl)-GLP-2(1-33);
L17K(4-(octadecanoylamino)butanoyl)-GLP-2(1-33);
L17K(4-(nonadecanoylamino)butanoyl)-GLP-2(1-33);
L17K(4-(eicosanoylamino)butanoyl)-GLP-2(1-33);
A18K(3-(hexadecanoylamino)propionyl)-GLP-2(1-33);
D21K(3-(hexadecanoylamino)propionyl)-GLP-2(1-33);
N24K(3-(hexadecanoylamino)propionyl)-GLP-2(1-33);
Q28K(3-(hexadecanoylamino)propionyl)-GLP-2(1-33);
S5K(3-(hexadecanoylamino)propionyl)/K30R-GLP-2(1-33);
S7K(3-(hexadecanoylamino)propionyl)/K30R-GLP-2(1-33);
D8K(3-(hexadecanoylamino)propionyl)/K30R-GLP-2(1-33);
E9K(3-(hexadecanoylamino)propionyl)/K30R-GLP-2(1-33);
M10K(3-(hexadecanoylamino)propionyl)/K30R-GLP-2(1-33);
N11K(3-(hexadecanoylamino)propionyl)/K30R-GLP-2(1-33);
T12K(3-(hexadecanoylamino)propionyl)/K30R-GLP-2(1-33);
I13K(3-(hexadecanoylamino)propionyl)/K30R-GLP-2(1-33);
L14K(3-(hexadecanoylamino)propionyl)/K30R-GLP-2(1-33);
D15K(3-(hexadecanoylamino)propionyl)/K30R-GLP-2(1-33);
N16K(3-(hexadecanoylamino)propionyl)/K30R-GLP-2(1-33);
L17K(3-(octanoylamino)propionyl)/K30R-GLP-2(1-33);
L17K(3-(nonanoylamino)propionyl)/K30R-GLP-2(1-33);
L17K(3-(decanoylamino)propionyl)/K30R-GLP-2(1-33);
L17K(3-(undecanoylamino)propionyl)/K30R-GLP-2(1-33);
L17K(3-(dodecanoylamino)propionyl)/K30R-GLP-2(1-33);
L17K(3-(tridecanoylamino)propionyl)/K30R-GLP-2(1-33);
L17K(3-(tetradecanoylamino)propionyl)/K30R-GLP-2(1-33);
L17K(3-(pentadecanoylamino)propionyl)/K30R-GLP-2(1-33);
L17K(3-(hexadecanoylamino)propionyl)/K30R-GLP-2(1-33);
L17K(3-(heptadecanoylamino)propionyl)/K30R-GLP-2(1-33);
L17K(3-(octadecanoylamino)propionyl)/K30R-GLP-2(1-33);
L17K(3-(nonadecanoylamino)propionyl)/K30R-GLP-2(1-33);
L17K(3-(eicosanoylamino)propionyl)/K30R-GLP-2(1-33);
L17K((S)-4-carboxy-4-(octanoylamino)butanoyl)/K30R-GLP-2(1-33);
L17K((S)-4-carboxy-4-(nonanoylamino)butanoyl)/K30R-GLP-2(1-33);
L17K((S)-4-carboxy-4-(decanoylamino)butanoyl)/K30R-GLP-2(1-33);
L17K((S)-4-carboxy-4-(undecanoylamino)butanoyl)/K30R-GLP-2(1-33);
L17K((S)-4-carboxy-4-(dodecanoylamino)butanoyl)/K30R-GLP-2(1-33);
L17K((S)-4-carboxy-4-(tridecanoylamino)butanoyl)/K30R-GLP-2(1-33);
L17K((S)-4-carboxy-4-(tetradecanoylamino)butanoyl)/K30R-GLP-2(1-33);
L17K((S)-4-carboxy-4-(pentadecanoylamino)butanoyl)/K30R-GLP-2(1-33);
L17K((S)-4-carboxy-4-(hexadecanoylamino)butanoyl)/K30R-GLP-2(1-33);
L17K((S)-4-carboxy-4-(heptadecanoylamino)butanoyl)/K30R-GLP-2(1-33);
L17K((S)-4-carboxy-4-(octadecanoylamino)butanoyl)/K30R-GLP-2(1-33);
L17K((S)-4-carboxy-4-(nonadecanoylamino)butanoyl)/K30R-GLP-2(1-33);
L17K((S)-4-carboxy-4-(eicosanoylamino)butanoyl)/K30R-GLP-2(1-33);
L17K(4-(octanoylamino)butanoyl)/K30R-GLP-2(1-33);
L17K(4-(nonanoylamino)butanoyl)/K30R-GLP-2(1-33);
L17K(4-(decanoylamino)butanoyl)/K30R-GLP-2(1-33);
L17K(4-(undecanoylamino)butanoyl)/K30R-GLP-2(1-33);
L17K(4-(dodecanoylamino)butanoyl)/K30R-GLP-2(1-33);
L17K(4-(tridecanoylamino)butanoyl)/K30R-GLP-2(1-33);
L17K(4-(tetradecanoylamino)butanoyl)/K30R-GLP-2(1-33);

L17K(4-(pentadecanoylamino)butanoyl)/K30R-GLP-2(1-33);
L17K(4-(hexadecanoylamino)butanoyl)/K30R-GLP-2(1-33);
L17K(4-(heptadecanoylamino)butanoyl)/K30R-GLP-2(1-33);
L17K(4-(octadecanoylamino)butanoyl)/K30R-GLP-2(1-33);
L17K(4-(nonadecanoylamino)butanoyl)/K30R-GLP-2(1-33);
L17K(4-eicosanoylamino)butanoyl)/K30R-GLP-2(1-33);
A18K(3-(hexadecanoylamino)propionyl)/K30R-GLP-2(1-33);
D21K(3-(hexadecanoylamino)propionyl)/K30R-GLP-2(1-33);
N24K(3-(hexadecanoylamino)propionyl)/K30R-GLP-2(1-33);
Q28K(3-(hexadecanoylamino)propionyl)/K30R-GLP-2(1-33);
D3E/S5K(3-(hexadecanoylamino)propionyl)/K30R/D33E-GLP-2(1-33);
D3E/S7K(3-(hexadecanoylamino)propionyl)/K30R/D33E-GLP-2(1-33);
D3E/D8K(3-(hexadecanoylamino)propionyl)/K30R/D33E-GLP-2(1-33);
D3E/E9K(3-(hexadecanoylamino)propionyl)/K30R/D33E-GLP-2(1-33);
D3E/M10K(3-(hexadecanoylamino)propionyl)/K30R/D33E-GLP-2(1-33);
D3E/N11K(3-(hexadecanoylamino)propionyl)/K30R/D33E-GLP-2(1-33);
D3E/T12K(3-(hexadecanoylamino)propionyl)/K30R/D33E-GLP-2(1-33);
D3E/I13K(3-(hexadecanoylamino)propionyl)/K30R/D33E-GLP-2(1-33);
D3E/L14K(3-(hexadecanoylamino)propionyl)/K30R/D33E-GLP-2(1-33);
D3E/D15K(3-(hexadecanoylamino)propionyl)/K30R/D33E-GLP-2(1-33);
D3E/N16K(3-(hexadecanoylamino)propionyl)/K30R/D33E-GLP-2(1-33);
D3E/L17K(3-(octanoylamino)propionyl)/K30R/D33E-GLP-2(1-33);
D3E/L17K(3-(nonanoylamino)propionyl)/K30R/D33E-GLP-2(1-33);
D3E/L17K(3-(decanoylamino)propionyl)/K30R/D33E-GLP-2(1-33);
D3E/L17K(3-(undecanoylamino)propionyl)/K30R/D33E-GLP-2(1-33);
D3E/L17K(3-(dodecanoylamino)propionyl)/K30R/D33E-GLP-2(1-33);
D3E/L17K(3-(tridecanoylamino)propionyl)/K30R/D33E-GLP-2(1-33);
D3E/L17K(3-(tetradecanoylamino)propionyl)/K30R/D33E-GLP-2(1-33);
D3E/L17K(3-(pentadecanoylamino)propionyl)/K30R/D33E-GLP-2(1-33);
D3E/L17K(3-(hexadecanoylamino)propionyl)/K30R/D33E-GLP-2(1-33);
D3E/L17K(3-(heptadecanoylamino)propionyl)/K30R/D33E-GLP-2(1-33);
D3E/L17K(3-(octadecanoylamino)propionyl)/K30R/D33E-GLP-2(1-33);
D3E/L17K(3-(nonadecanoylamino)propionyl)/K30R/D33E-GLP-2(1-33);
D3E/L17K(3-(eicosanoylamino)propionyl)/K30R/D33E-GLP-2(1-33);
D3E/L17K((S)-4-carboxy-4-(octanoylamino)butanoyl)/K30R/D33E-GLP-2(1-33);
D3E/L17K((S)-4-carboxy-4-(nonanoylamino)butanoyl)/K30R/D33E-GLP-2(1-33);
D3E/L17K((S)-4-carboxy-4-(decanoylamino)butanoyl)/K30R/D33E-GLP-2(1-33);
D3E/L17K((S)-4-carboxy-4-(undecanoylamino)butanoyl)/K30R/D33E-GLP-2(1-33);
D3E/L17K((S)-4-carboxy-4-(dodecanoylamino)butanoyl)/K30R/D33E-GLP-2(1-33);
D3E/L17K((S)-4-carboxy-4-(tridecanoylamino)butanoyl)/K30R/D33E-GLP-2(1-33);
D3E/L17K((S)-4-carboxy-4-(tetradecanoylamino)butanoyl)/K30R/D33E-GLP-2(1-33);
D3E/L17K((S)-4-carboxy-4-(pentadecanoylamino)butanoyl)/K30R/D33E-GLP-2(1-33);
D3E/L17K((S)-4-carboxy-4-(hexadecanoylamino)butanoyl)/K30R/D33E-GLP-2(1-33);
D3E/L17K((S)-4-carboxy-4-(heptadecanoylamino)butanoyl)/K30R/D33E-GLP-2(1-33);
D3E/L17K((S)-4-carboxy-4-(octadecanoylamino)butanoyl)/K30R/D33E-GLP-2(1-33);
D3E/L17K((S)-4-carboxy-4-(nonadecanoylamino)butanoyl)/K30R/D33E-GLP-2(1-33);
D3E/L17K((S)-4-carboxy-4-(eicosanoylamino)butanoyl)/K30R/D33E-GLP-2(1-33);
D3E/L17K(4-(octanoylamino)butanoyl)/K30R/D33E-GLP-2(1-33);
D3E/L17K(4-(nonanoylamino)butanoyl)/K30R/D33E-GLP-2(1-33);
D3E/L17K(4-(decanoylamino)butanoyl)/K30R/D33E-GLP-2(1-33);
D3E/L17K(4-(undecanoylamino)butanoyl)/K30R/D33E-GLP-2(1-33);
D3E/L17K(4-(dodecanoylamino)butanoyl)/K30R/D33E-GLP-2(1-33);
D3E/L17K(4-(tridecanoylamino)butanoyl)/K30R/D33E-GLP-2(1-33);
D3E/L17K(4-(tetradecanoylamino)butanoyl)/K30R/D33E-GLP-2(1-33);
D3E/L17K(4-(pentadecanoylamino)butanoyl)/K30R/D33E-GLP-2(1-33);
D3E/L17K(4-(hexadecanoylamino)butanoyl)/K30R/D33E-GLP-2(1-33);
D3E/L17K(4-(heptadecanoylamino)butanoyl)/K30R/D33E-GLP-2(1-33);
D3E/L17K(4-(octadecanoylamino)butanoyl)/K30R/D33E-GLP-2(1-33);
D3E/L17K(4-(nonadecanoylamino)butanoyl)/K30R/D33E-GLP-2(1-33);
D3E/L17K(4-(eicosanoylamino)butanoyl)/K30R/D33E-GLP-2(1-33);
D3E/A18K(3-(hexadecanoylamino)propionyl)/K30R/D33E-GLP-2(1-33);
D3E/D21K(3-(hexadecanoylamino)propionyl)/K30R/D33E-GLP-2(1-33);
D3E/N24K(3-(hexadecanoylamino)propionyl)/K30R/D33E-GLP-2(1-33); and
D3E/Q28K(3-(hexadecanoylamino)propionyl)/K30R/D33E-GLP-2(1-33).

Methods for the preparation of GLP-2, analogs thereof as well as GLP-2 derivatives can be found in e.g. WO 99/43361 and WO 00/55119.

In a further embodiment of the invention the glucagon-like peptide is an insulinotropic analog of exendin-4(1-39), e.g. Ser$^2$Asp$^3$-exendin-4(1-39) wherein the amino acid residues in position 2 and 3 have been replaced with serine and aspartic acid, respectively (this particular analog also being known in the art as exendin-3).

In a further embodiment of the invention the glucagon-like peptide is an exendin-4 derivative wherein the substituent introduced is selected from amides, carbohydrates, alkyl groups, esters and lipophilic substituents. An example of an insulinotropic derivatives of exendin-4(1-39) and analogs thereof is $Tyr^{31}$-exendin-4(1-31)-amide.

In another embodiment of the invention the glucagon-like peptide is a stable exendin-4 compound. In another embodiment of the invention the glucagon-like peptide is a DPP-IV protected exendin-4 compound. In another embodiment of the invention the glucagon-like peptide is an immunomodulated exendin-4 compound.

Methods for the preparation of exendin-4, analogs thereof as well as exendin-4 derivatives can be found in e.g. WO 99/43708, WO 00/41546 and WO 00/55119.

The parent glucagon-like peptide can be produced by peptide synthesis, e.g. solid phase peptide synthesis using Boc-chemistry or other well established techniques. The parent glucagon-like peptide can also be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the peptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae,* or mammalian BHK or CHO cell lines.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

In the following examples "Compound 1" is intended to mean: $Arg^{34},Lys^{26}(N^{\epsilon}(\gamma\text{-}Glu(N^{\alpha}\text{-}hexadecanoyl)))$-GLP-1 (7-37)

General Procedure 1

Preservative, isotonic agent and buffer were dissolved in water and pH adjusted to 7.4. Compound 1 was dissolved in water while stirring slowly. The two solutions were mixed and pH adjusted to 7.4 using Sodium Hydroxide and/or Hydrochloric Acid. Finally, the formulation was filtered through a 0.22 μm filter.

General Procedure 2

Preservative, isotonic agent, buffer and serum albumin were dissolved in water and pH adjusted to 7.4. Compound 1 was dissolved in water while stirring slowly. The two solutions were mixed and pH adjusted to 7.4 using Sodium Hydroxide and/or Hydrochloric Acid. Finally, the formulation was filtered through a 0.22 µm filter.

Physical stability of the formulations is evaluated by means of a stressed test. The stressed test is performed as a rotation test. 50 µL air is added to 5 cartridges (glass vials) of each formulation. The cartridges are stored at 37° C. and rotated with a frequency of 30 rotations per minute for 4 hours daily. The test was stopped after 28 days of rotation. The visual inspection of the cartridges is followed daily or as required. Visual inspection of the formulations is performed in a sharp focused light with a dark background. The turbidity of the formulation is characterized by a visual score ranking the degree of turbidity from 0 to 3 (a formulation showing no turbidity corresponds to a visual score 0, and a formulation showing visual turbidity in daylight corresponds to visual score 3). A formulation is classified as physical unstable with respect to protein aggregation, when it shows visual turbidity in daylight.

The number of days in the rotation test until visual turbidity in daylight was seen (corresponding to visual score 3) are given in Table 1 (mean of 5 cartridges):

TABLE 1

Assessment of stability of formulations prepared according to the general procedures.

| Example | Concentration of Compound 1 | Concentration of serum albumin | pH | Days until visual turbidity in daylight was seen |
|---|---|---|---|---|
| 1 | 3 mg/ml | 0 | 7.4 | 7 |
| 2 | 3 mg/ml | 0.1% human serum albumin | 7.4 | 28 |
| 3 | 3 mg/ml | 1% human serum albumin | 7.4 | 27 |
| 4 | 3 mg/ml | 0.1% recombinant serum albumin | 7.4 | 22 |
| 5 | 3 mg/ml | 1% recombinant serum albumin | 7.4 | 26 |

It is seen that the formulations containing serum albumin is more physically stable compared to the reference without serum albumin.

Another method to test the physical stability is the Thioflavin T-test. The physical stability of the different formulations is characterized by their tendency to form fibrils. A method to determine the presence of fibrils is the Thioflavin T-test. The histological thiazole dye Thioflavin T (ThT) is used as an indicator of amyloid fibril formation. The method is based on the fluorescent characteristics of ThT. In the presence of amyloid fibrils, the fluorescense of ThT exhibits an excitation maximum at 450 nm and enhanced emission at 482 nm. The ThT fluorescence intensity has been shown to be linear with the increase in amyloid fibril concentration. The physical stability of the formulations is evaluated by the ThT-test after storage of the formulation in top filled glass cartridges for various time periods.

The results from ThT-test after 3 months storage at 37° C. can be seen in Table 2. It is seen that the formulations containing serum albumin is more physically stable compared to the reference without serum albumin.

TABLE 2

Results from ThT-test after 3 months storage at 37° C.

| Example | Concentration of Compound 1 | Concentration of serum albumin | pH | Fluorescence units |
|---|---|---|---|---|
| 1 | 3 mg/ml | 0 | 7.4 | 73.0 |
| 2 | 3 mg/ml | 0.1% human serum albumin | 7.4 | 17.9 |
| 3 | 3 mg/ml | 1% human serum albumin | 7.4 | 46.4 |
| 4 | 3 mg/ml | 0.1% recombinant serum albumin | 7.4 | 24.2 |
| 5 | 3 mg/ml | 1% recombinant serum albumin | 7.4 | 34.1 |

The purity of the different formulations is measured by RP-HPLC (see Table 3). It is seen purity is maintained in the presence of serum albumin.

TABLE 3

Purity of formulations measured by RP-HPLC.

| Example | Concentration of Compound 1 | Concentration of serum albumin | pH | Purity (%) |
|---|---|---|---|---|
| 1 | 3 mg/ml | 0 | 7.4 | 99.2 |
| 2 | 3 mg/ml | 0.1% human serum albumin | 7.4 | 99.0 |
| 3 | 3 mg/ml | 1% human serum albumin | 7.4 | 98.0 |
| 4 | 3 mg/ml | 0.1% recombinant serum albumin | 7.4 | 99.2 |
| 5 | 3 mg/ml | 1% recombinant serum albumin | 7.4 | 98.0 |

The invention claimed is:

1. A pharmaceutical composition for parenteral administration, said composition comprising a glucagon-like peptide, human serum albumin or a variant thereof, a pharmaceutically acceptable buffer, a pharmaceutically acceptable preservative, and optionally an isotonicity agent and/or a stabilizer, wherein the pH of said pharmaceutical composition is from pH 7.2 to pH 8.0, and wherein the concentration of said glucagon-like peptide is from 3.0 mg/ml to 50 mg/ml.

2. The pharmaceutical composition according to claim 1, wherein the composition is a solution.

3. The pharmaceutical composition according to claim 1, wherein the composition is a suspension.

4. The pharmaceutical composition according to claim 1, which is a solid.

5. The pharmaceutical composition according to claim 4, which is to be reconstituted with water or another suitable solvent for injection.

6. The pharmaceutical composition according to claim 1, which is suitable for administration by injection or infusion.

7. The pharmaceutical composition according to claim 1, which is suitable for subcutaneous administration.

8. The pharmaceutical composition according to claim 1, which is suitable for intramuscular administration.

9. A pharmaceutical composition according to claim 1, which is suitable for intravenous administration.

10. The pharmaceutical composition according to claim 1, wherein said human serum albumin or a variant thereof is produced by recombinant DNA technology.

11. The pharmaceutical composition according to claim 1, wherein said human serum albumin or a variant thereof is a human serum albumin variant.

12. The pharmaceutical composition according to claim 11, wherein said human serum albumin variant has reduced binding affinities towards copper and nickel as compared to the corresponding binding affinities of human serum albumin towards copper and nickel.

13. The pharmaceutical composition according to claim 11, wherein said human serum albumin variant is a fragment of human serum albumin.

14. The pharmaceutical composition according to claim 11, wherein said human serum albumin variant comprises a modification of the Asp-Ala-His-Lys N-terminal sequence of human serum albumin.

15. The pharmaceutical composition according to claim 14, wherein said human serum albumin variant comprises at least one amino acid deletion among the three N-terminal amino acid residues Asp-Ala-His in the N-terminal of human serum albumin.

16. The pharmaceutical composition according to claim 14, wherein said modification of the Asp-Ala-His-Lys N-terminal sequence of human serum albumin is an N-terminal extension, such as $Glu^{-3}$, $Ala^{-2}$, $Glu^{-1}$, $Phe^{0}$-HSA(1-585) or an N-terminal fragment thereof.

17. The pharmaceutical composition according to claim 14, wherein said human serum albumin variant is selected from the group consisting of HSA(2-585), HSA(3-585), HSA(4-585), Asp-Ala-HSA(4-585), Xaa3-HSA(1-585) where $Xaa^3$ is an amino acid residue which has substituted the His residue occupying position 3 in native HSA, and fragments thereof.

18. The pharmaceutical composition according to claim 1, wherein the concentration of human serum albumin or a variant thereof is less than 10% w/v.

19. The pharmaceutical composition according to claim 1, wherein the isoelectric point of said glucagon-like peptide is from 3.0 to 7.0.

20. The pharmaceutical composition according to claim 1, wherein said glucagon-like peptide is GLP-1, a GLP-1 analogue, a derivative of GLP-1 or a derivative of a GLP-1 analogue.

21. The pharmaceutical composition according to claim 20, wherein said GLP-1 analogue is selected from the group consisting of:

$Gly^8$-GLP-1(7-36)-amide,
$Gly^8$-GLP-1(7-37),
$Val^8$-GLP-1(7-36)-amide,
$Val^8$-GLP-1(7-37),
$Val^8Asp^{22}$-GLP-1(7-36)-amide,
$Val^8Asp^{22}$-GLP-1(7-37),
$Val^8Glu^{22}$-GLP-I(7-36)-amide,
$Val^8Glu^{22}$-GLP-1(7-37),
$Val^8Lys^{22}$-GLP-I(7-36)-amide, Val⁸Lys²²-GLP-1(7-37),
Val⁸Arg²²-GLP-1(7-36)-amide,
Val⁸Arg²²-GLP-1(7-37),
Val⁸His²²-GLP-1(7-36)-amide,
Val⁸His²²-GLP-1(7-37),
Val⁸Trp¹⁹Glu²²-GLP-1(7-37),
Val⁸Glu²²Val²⁵-GLP-1(7-37),
Val⁸Tyr¹⁶Glu²²-GLP-1(7-37),
Val⁸Trp¹⁶Glu²²-GLP-1(7-37),
Val⁸Leu¹⁶Glu²²-GLP-1(7-37),
Val⁸Tyr¹⁸Glu²²-GLP-1(7-37),
Val⁸Glu²²His³⁷-GLP-1(7-37),
Val⁸Glu²²Ile³³-GLP-1(7-37),
Val⁸Trp¹⁶Glu²²Val²⁵Ile³³-GLP-1(7-37),
Val⁸Trp¹⁶Glu²²Ile³³-GLP-1(7-37),
Val⁸Glu²²Val²⁵Ile³³-GLP-1(7-37),
Val⁸Trp¹⁶Glu²²Val²⁵-GLP-1(7-37),
and analogues thereof and derivatives of any of these.

22. The pharmaceutical composition according to claim 20, wherein said glucagon-like peptide has from 31 to 43 amino acid residues.

23. The pharmaceutical composition according to claim 1, wherein said derivative of GLP-1 or a derivative of a GLP-1 analogue has a lysine residue, wherein a lipophilic substituent optionally via a spacer is attached to the epsilon amino group of said lysine.

24. The pharmaceutical composition according to claim 23, wherein said lipophilic substituent has from 8 to 40 carbon atoms.

25. The pharmaceutical composition according to claim 23, wherein said spacer is present and is selected from an amino acid selected from the group consisting of beta-Ala, L-Glu, and aminobutyroyl.

26. The pharmaceutical composition according to claim 23, wherein said derivative of a GLP-1 analogue is Arg³⁴, Lys²⁶(Nᵉ-(5,γ-Glu(Nᵃ-hexadecanoyl)))-GLP⁻1(7-37).

27. The pharmaceutical composition according to claim 1, wherein said glucagon-like peptide is a DPPIV-protected glucagon-like peptide.

28. The pharmaceutical composition according to any claim 1, wherein said glucagon-like peptide is a plasma stable glucagon-like peptide.

29. The pharmaceutical composition according to claim 1, wherein said glucagon-like peptide is GLP-2, a GLP-2 analogue, a derivative of GLP-2 or a derivative of a GLP-2 analogue.

30. The pharmaceutical composition according to claim 29, wherein said derivative of GLP-2 or a derivative of a GLP-2 analogue has a lysine residue, such as one lysine, wherein a lipophilic substituent optionally via a spacer is attached to the epsilon amino group of said lysine.

31. The pharmaceutical composition according to claim 30, wherein said lipophilic substituent has from 8 to 40 carbon atoms.

32. The pharmaceutical composition according to claim 30, wherein said spacer is present and is selected from an amino acid selected from the group consisting of beta-Ala, L-Glu, and aminobutyroyl.

33. The pharmaceutical composition according to claim 29, wherein said glucagon-like peptide has from 27 to 39 amino acid residues.

34. The pharmaceutical composition according to claim 29, wherein the concentration of said glucagon-like peptide is from 0.1 mg/ml to 100 mg/ml.

35. The pharmaceutical composition according to claim 1, wherein said glucagon-like peptide is exendin-4, an exendin-4 analogue, a derivative of exendin-4, or a derivative of an exendin-4 analogue.

36. The pharmaceutical composition according to claim 35, wherein said glucagon-like peptide is exendin-4.

37. The pharmaceutical composition according to claim 35, wherein said derivative of exendin-4 or derivative of an exendin-4 analogue is acylated or pegylated.

38. The pharmaceutical composition according to claim 35, wherein said derivative of exendin-4 or derivative of an exendin-4 analogue has a lysine residue, such as one lysine, wherein a lipophilic substituent optionally via a spacer is attached to the epsilon amino group of said lysine.

39. The pharmaceutical composition according to claim 38, wherein said lipophilic substituent has from 8 to 40 carbon atoms.

40. The pharmaceutical composition according to claim 38, wherein said spacer is present and is selected from an amino acid selected from the group consisting of beta-Ala, L-Glu, and aminobutyroyl.

41. The pharmaceutical composition according to claim 35, wherein said glucagon-like peptide has from 30 to 48 amino acid residues.

42. The pharmaceutical composition according to claim 35, wherein the concentration of said glucagon-like peptide is from 5 μg/ml to 10 mg/ml.

43. The pharmaceutical composition according to claim 1, wherein said glucagon- like peptide is glucagon, a glucagon analogue or a derivative thereof.

44. The pharmaceutical composition according to claim 1, wherein said glucagon-like peptide is Arg³⁴, Lys²⁶(Nᵉ-(5,γ-Glu(Nᵃ-hexadecanoyl)))-GLP-I(7-37) and said human serum albumin or a variant thereof is recombinant human serum albumin.

45. The pharmaceutical composition according to claim 44, wherein the concentration of Arg³⁴, Lys²⁶(Nᵉ-(5, γ-Glu(Nᵃ-hexadecanoyl)))-GLP-1(7-37) is in the range from 3 mg/ml to 8 mg/ml and the concentration of recombinant human serum albumin is in the range from 0.001% w/v to 10% w/v.

46. The pharmaceutical composition according to claim 1, wherein said buffer is ortho-phosphate, TRIS, glycine, N-glycylglycine, citrate sodium acetate, sodium carbonate, glycylglycine, histidine, lysine, arginine, sodium phosphate, and sodium citrate or mixtures thereof.

47. The pharmaceutical composition according to claim 1, wherein said preservative is phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof.

48. The pharmaceutical composition according to claim 1, wherein said isotonicity agent is present.

49. The pharmaceutical composition according to claim 48, wherein said isotonicity agent is sodium chloride, xylitol, mannitol, sorbitol, glycerol, glucose, maltose, sucrose, L-glycine, L-histidine, arginine, lysine, isoleucine, aspartic acid, tryptophan, threonine, polyethyleneglycol, propylene glycol or mixtures thereof.

50. The pharmaceutical composition according to claim 1, which further comprises a stabiliser.

51. The pharmaceutical composition according to claim 1, which further comprises a surfactant.

52. A method for treatment of hyperglycemia comprising parenteral administration of an effective amount of the pharmaceutical composition according to claim 1.

* * * * *

UNITED STATES PATENT AND TRADEMARK OFFICE
CERTIFICATE OF CORRECTION

PATENT NO.        : 7,595,293 B2                                          Page 1 of 1
APPLICATION NO.   : 11/244497
DATED             : September 29, 2009
INVENTOR(S)       : Engelund et al.

It is certified that error appears in the above-identified patent and that said Letters Patent is hereby corrected as shown below:

Column 23, line 37: delete "5,".

Column 24, line 30: delete "5,".

Column 24, line 35: delete "5,".

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO.       : 7,595,293 B2                             Page 1 of 1
APPLICATION NO. : 11/244497
DATED            : September 29, 2009
INVENTOR(S)      : Engelund et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 498 days.

Signed and Sealed this

Twenty-eighth Day of September, 2010

David J. Kappos
*Director of the United States Patent and Trademark Office*